United States Patent [19]

Glenn et al.

[11] 3,958,559

[45] May 25, 1976

[54] ULTRASONIC TRANSDUCER

[75] Inventors: William E. Glenn, Stamford; Anant K. Nigam, Fairfield, both of Conn.

[73] Assignee: New York Institute of Technology, Old Westbury, N.Y.

[22] Filed: Oct. 16, 1974

[21] Appl. No.: 515,352

[52] U.S. Cl. .............................. 128/2 V; 73/67.5 R; 73/71.5 US; 128/24 A; 128/303 R; 310/8.3; 340/8 L
[51] Int. Cl.² .................... A61B 10/00; H01L 41/10
[58] Field of Search ............ 128/2 V, 2.05 Z, 24 A, 128/362, 395; 340/8 L; 73/67.8 R, 67.8 S, 67.9, 71.5 US, 67.5; 350/190; 310/8.2, 8.3; 181/.5

[56] References Cited
UNITED STATES PATENTS

| | | | |
|---|---|---|---|
| 2,477,246 | 7/1949 | Gillespie | 340/8 L |
| 2,968,302 | 1/1961 | Fry et al. | 128/24 A |
| 3,237,623 | 3/1966 | Gordon | 128/24 A |
| 3,358,677 | 12/1967 | Sheldon | 128/24 A |
| 3,587,561 | 6/1971 | Ziedonis | 128/2.05 Z |
| 3,618,696 | 11/1971 | Hurwitz | 340/8 L |
| 3,699,805 | 10/1972 | Bayre | 340/8 L |
| 3,771,355 | 11/1973 | Sachs | 128/2 V |

*Primary Examiner*—Kyle L. Howell
*Attorney, Agent, or Firm*—Martin Novack

[57] ABSTRACT

For use in ultrasound pulse-echo imaging and neurosurgery systems, a plano-concave lens of elliptical shape is positioned in front of a transducer for producing an extremely narrow ultrasonic beam, and at the same time provides a large aperture to maximize the ultrasound power output from the transducer and the capture angle of reflected echoes. The lens is preferably formed of plastic, selected from a wide variety of available plastics in accordance with desired acoustical properties for a given application, and is preferably bonded to a flat, disc-shaped transducer. By proper selection of the material used to construct the lens it is possible to produce the correct amount of transducer apodization.

9 Claims, 3 Drawing Figures

U.S. Patent    May 25, 1976    3,958,559
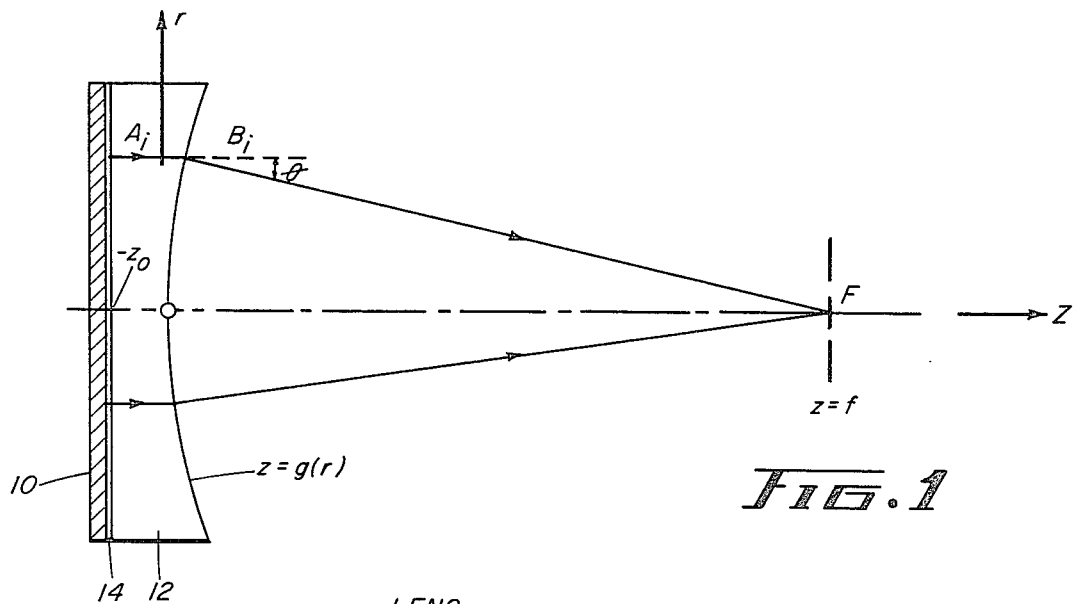
$\overline{FIG}.1$
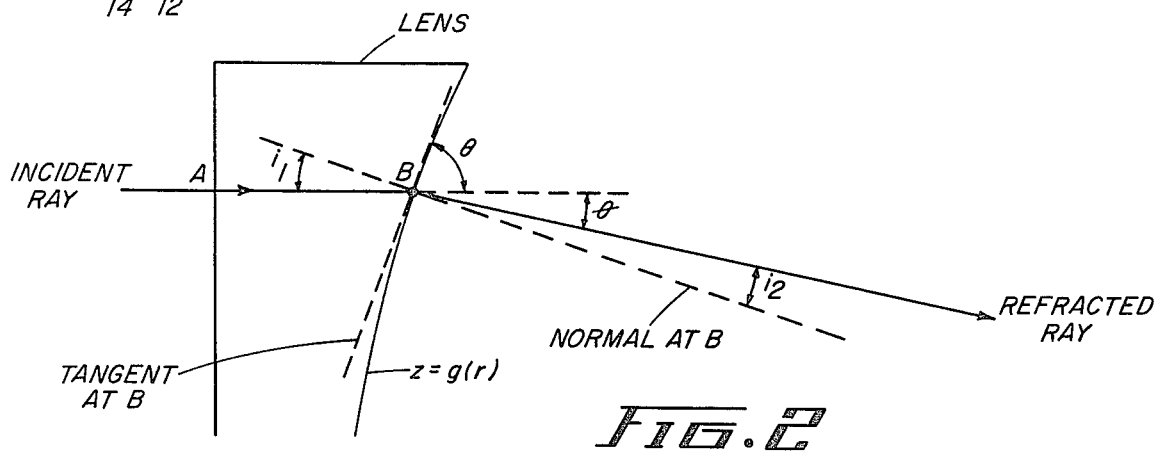
$\overline{FIG}.2$
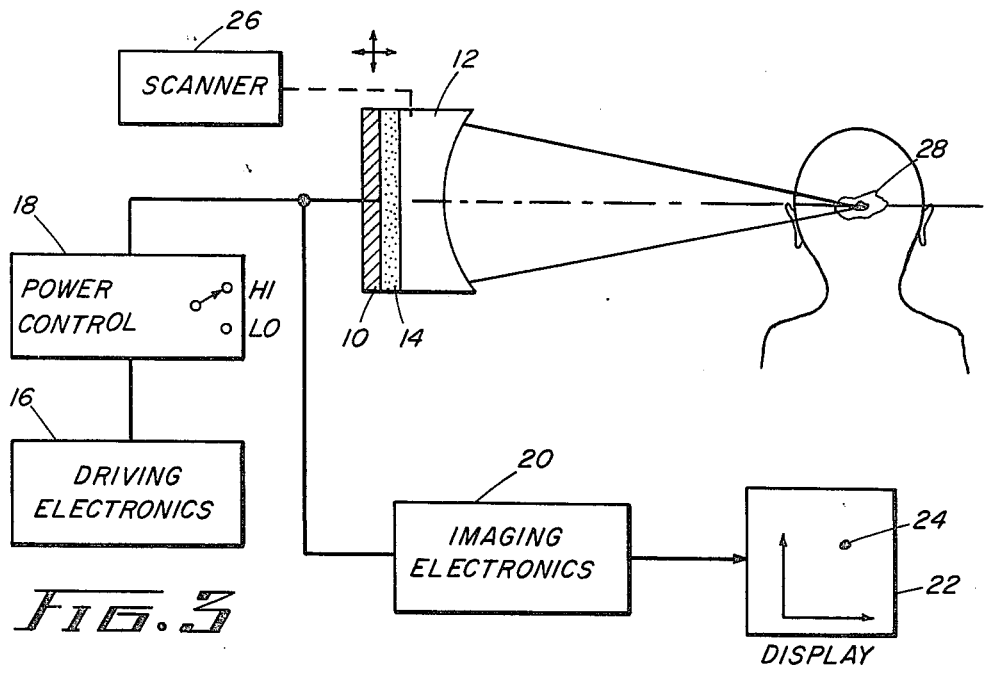
$\overline{FIG}.3$

ULTRASONIC TRANSDUCER

BACKGROUND OF THE INVENTION

This invention relates to ultrasonic techniques for exploring internal structures and non-invasive treatment of internal structures, and more particularly to an improved transducer and lens combination for generating narrow cross-section ultrasound beams for use in pulse-echo imaging and ultrasonic neurosurgical systems.

In recent years considerable progress has been made in the utilization of ultrasonic techniques for the exploration of the internal structure of living organisms. This technique has been used to measure and record the dimensions and position of deep-lying organs, and physiological structures throughout the body. An important advantage of ultrasonics is that it is non-destructive at power levels for pulse-echo imaging and free of the hazards incident to the use of x-ray or gamma ray examination, yet useful at higher ultrasound power levels focussed at a desired point within the body (at the location of a tumor, for example) in "burning out" and destroying the tumor without serious damage to surrounding tissue.

In the exploratory or pulse-echo imaging technique, a series of very short ultrasonic pulses is projected in a narrow, straight beam in the direction to be viewed. For this purpose, a transducer is coupled to the skin with a cream or fluid, and measurements are based on the amount of time for an echo to return to the transducer and also on the amplitude of the echo. Such echoes are produced from biologic structures which present a different acoustic impedance to the traveling pulses. Interfaces reflect not only if they are of different density, but also if they are of different elasticity.

A variety of procedures are known for producing patterns on a cathode ray viewing screen representative of the internal structure being scanned. Echo pulses may be displayed on an "A" cathode-ray indicator, the echo pulses from the different reflecting targets being displayed as "pips" of varying height along the time base sweep line on a screen. The height of each pip is indicative of the relative reflectivity of the target, whereas the displacement of the pip with respect to the point of origin of the sweep lines is indicative of the distance between the target and the transducer. In the known "B" type scan, the electron beam of the cathode-ray indicator is intensity-modulated by returning echoes as the transducer beam is shifted across a particular area of the body, and the electron beam is deflected in synchronism therewith. In this presentation, the view is similar to a cross-section taken at right angles to the axis of the transducer. Thus, it is possible with either of these scanning techniques to definitely determine the depth coordinate of an internal structure, such as a tumor, which exhibits different reflectivity than the surrounding tissue, the degree of definiteness of location of the internal structure being dependent on the imaging resolution of the system which, in turn, is proportional to the cross-section of the ultrasonic beam.

Once the coordinates of the internal structure are determined by pulse-echo imaging techniques, it is known that ultrasound energy precisely focussed on the internal structure can destroy the structure and produce a lesion of a predetermined volume, which, again, is proportional to the cross-section of the ultrasonic beam. For proper determination of the depth coordinates and the formation of a lesion volume sufficiently small to preclude damage to surrounding tissue, extremely narrow beams of less than 0.5mm diameter are required. This required beam size approaches the wavelength of the transmitted ultrasound waves, and, accordingly, unless a shaped transducer or a lens is used, diffraction effects limit the minimum beam size to about 5 to 10mm. Moreover, it is desirable that the transducer have as large an aperture as possible to maximize the capture angle of the reflected echoes and/or to maximize the ultrasound power output. However, it is virtually impossible in the current state of the art of piezoceramic transducers to construct a large aperture transducer of proper shape to produce an ultrasonic beam of the required small diameter, and if construction of such shaped transducers were possible, the cost would be prohibitive. Available machining and polishing techniques make it much easier to fabricate flat, disc-shaped, large aperture piezoceramic transducers, and attempt to employ a lens in conjunction therewith to achieve the desired beam cross-section.

Earlier studies reported in the literature have investigated the focusing properties of spherical lenses with the objective of keeping the aberrations to a minimum over large angular fields-of-view of the lens, which has entailed the design of doublet, triplet and other multi-element lens combinations using lens materials of various refractive indices. Although such lens combinations improve the quality of off-axis imaging, the designs are very expensive to implement, and moreover, when used in conventional reflective ultrasound imaging, the several interfaces of the multi-element lens lead to multiple reflections which cause artifacts in the image. From what has been said earlier, in known ultrasonic imaging and non-invasive surgical systems, the need is for extremely narrow on-axis beams, and it matters little what happens to the quality of the ultrasound radiation off-axis. The present invention provides the necessary small beam cross-section by the use of an ellipsoidalshaped lens in conjunction with a flat, disk-shaped transducer.

In the optical domain, the use of elliptical geometry to obtain aberration-free on-axis focusing was described by Descartes in 1637, a few years after Snell had stated the Law of Refraction; however, such lenses could not be tested, even in optical systems, due to the complexities in machining an ellipsoidal surface with the necessary tolerances of less than one quarter of the wavelength of light. The wavelengths generally associated with diagnostic ultrasound are in the range of 0.05 to 1.5mm. Employing state-of-the-art conventional machining processes it is possible to construct ellipsoidal lenses with surface tolerances much less than the wavelength of ultrasound. This being the case, and in view of the requirements of sharp on-axis focussing in pulse-echo imaging and non-invasive surgery systems, it is found that the ellipsoidal lens is best suited for such applications.

BRIEF SUMMARY OF THE INVENTION

According to the invention, a plano-concave lens of elliptical shape is placed in front of a flat, discshaped transducer. The lens is preferably formed of plastic, and since most plastics used for ultrasound lens construction vary widely in their ultrasound attenuating characteristics, and offer a wide selection of refractive indices, it is readily possible to select the plastic material which gives the desired focal length as well as the correct amount of apodization. An elliptical lens of a given geometry is free of spherical aberration, and it is possible to obtain a 0.5mm spot-size with, for example, an F/2 ellipsoidal lens at a frequency of 7MHz.

DESCRIPTION OF THE DRAWINGS

A better understanding of the invention will be had from the following detailed description, taken in conjunction with the accompanying drawings, in which:

FIGS. 1 and 2 are diagrams useful in explaining the efficacy of a lens of plano-concave shape for focusing ultrasonic energy; and FIG. 3 is a schematic diagram of a simplified pulse-echo diagnostic and non-invasive surgical system utilizing the improved transducer.

DESCRIPTION OF THE PREFERRED EMBODIMENT

Referring now to FIG. 1, the transducer according to the invention comprises an ultrasound transducer 10 of conventional flat disc-like geometry which by itself transmits an essentially collimated beam of ultrasound, in front of which is placed a plano-concave lens 12, the curved surface of which is of ellipsoidal shape. The lens is coupled to the transducer either by bonding or interposition of a layer 14 of a suitable coupling medium such as water, oil, or the like, as is well known in the art. It will be understood that FIG. 1 represents a cross-section in a plane perpendicular to and including the axis of the lens.

Designating $z$ and $r$ as the coordinates of the lens along the axis and radius, respectively, let $$z = g(r) \qquad \text{Eq. 1}$$

represent the curved surface of the lens, and let $c_1$ and $c_0$ represent the ultrasound velocities (in dilatation) for the lens material and the medium, respectively.

It is required that the various path-lengths $A_iB_iF$ are equal in the time domain; i.e., $$\frac{z_0 + g}{c_1} + \frac{[(f-g)^2 + r^2]^{\frac{1}{2}}}{c_0} = \frac{z_0}{c_1} + \frac{f}{c_0} \qquad \text{Eq. 2a}$$

or $$(1-n^2)g^2 - 2f(1-n)g + r^2 = 0 \qquad \text{Eq. 2b}$$

where $n = c_1/c_0$ is the index of refraction of the lens material with respect to water. The expression above is the ellipse $$\frac{(z-a)^2}{a^2} + \frac{r^2}{b^2} = 1 \qquad \text{Eq. 3}$$

where
$$a = f/(1+n)$$

$$b = f \left[ \frac{(1-n)}{(1+n)} \right]^{\frac{1}{2}}$$

It is additionally required that the various ray-paths $A_iB_iF$ satisfy Snell's Law at the curved surface. Employing the nomenclature of FIG. 2, one can express this condition mathematically:

$$g' \left[ \frac{g_1 - n}{g_1 + ng'^2} \right] = \frac{r}{f - g} \qquad \text{Eq. 4}$$

$$g' = \frac{d}{dr}(g), \text{ and}$$

$$g_1 = [1 + g'^2 (1 - n^2)]^{\frac{1}{2}} \qquad \text{Eq. 5}$$

Solving Eq. 2 for $g$ and substituting in Eq. 4, it is seen that the elliptical surface of Eq. 2 does indeed satisfy Eq. 4, and thereby Snell's law at the lens surface.

The above analysis shows than an ellipsoidal lens is free of spherical aberration. Thus, the focal zone $\Delta f$ (that zone in which the on-axis intensity level is greater than 0.5db below the maximum level at the focus) and the focal spot $\delta_f$ are given by $$\Delta f = 3f_{\#}^2 \lambda \qquad \text{Eq. 6}$$
$$\delta_f = 1.22 \lambda f_{\#} \qquad \text{Eq. 7}$$

where $f_{\#}$ is the numerical aperture and $\lambda$ is the wavelength of sound. It will be evident from these equations that a 0.5mm spot size can be attained by a F/2 elliptical lens at 7MHz.; the focal zone for this lens is about 3.6mm and the capture angle is $\pm \sin^{-1}(\frac{1}{2}f_{\#}) = \pm 15°$.

The focal spot $\delta_f$ in Eq. 7 is arrived at by uniform ultrasound intensity across the front surface of the lens, the equation of which is $$z = a [1 - \sqrt{1 - r^2/b^2}] \qquad \text{Eq. 3}$$

The actual obtainable resolution is generally less than $\delta_f$, however, because Eq. the presence of side lobes. The side lobes can be significantly reduced by transducer apodization, which may be accomplished in the fabrication of the lens itself. Most materials used for ultrasound lens construction, such as plastics, metals and liquids, vary widely in their ultrasound attenuating characteristics, and also offer a wide selection of refractive indices. With apodization, the incident ultrasound intensity at the front of the lens instead of being uniform over the face area of the lens may have a Gaussian or some other desired distribution. While the effect of any particular velocity distribution over the face of the lens can be investigated, by way of example, calculations are given below for the case when the desired distribution is Gaussian, for which $$w(r) \propto e^{-r^2/R^2} \qquad \text{Eq. 8}$$

where $w$ is the velocity distribution and $R$ is the characteristic parameter of the Gaussian distribution. Classical wave-propagation analyses can be employed for determining the distribution of the energy at the focal plane, but for brevity only the results are summarized here. Such analyses show that the sidelobes are almost completely suppressed if one requires that $$R = s A \qquad \text{Eq. 9}$$

with
$$1.5 \leq s \leq 0.5 \qquad \text{Eq. 10}$$

where $A$ is the half aperture of the elliptical lens. For $s < 0.5$, the sidelobes are better suppressed but the lens gain is reduced, whereas for $s > 1.5$ the suppression of the sidelobes is not completely adequate. For a particular lens design, therefore, the degree of apodization required is determined by the numerical value of $s$, which is at the choice of the designer in accordance with the required performance.

Assuming a Gaussian distribution and application of the transducer in a pulse-echo system, the choice of a lens material having the correct attenuation coefficient $\alpha$ requires that the following equality be satisfied:

$$e^{-2\alpha z} \propto e^{-r^2/R^2} \qquad \text{Eq. 10}$$

Assuming an $f_\#$ greater than 1, and substituting from Eq. 3 and solving, one obtains $$\alpha \doteq \frac{8.6 b^2}{a s^2 A^2} \text{db/cm}$$

$$\doteq 2 f_\# \frac{8.68(1-n)}{s^2 A} \text{db/cm} \qquad \text{Eq. 11}$$

Thus, for a 10 cm diameter transducer operating at a frequency of 5MHz. and employing an F/3 elliptical lens ($f_\# = 3$) with $s=1.0$, one has $$\alpha \doteq 10.42 (1-n) \text{ db/cm} \qquad \text{Eq. 12}$$

The lens material should possess the refractive index and attenuation which simultaneously satisfy Eq. 12. The commercially available material known as Nylon 101 has an attenuation $\alpha$ of about 4.7 db/cm at 5MHz. and a refractive index $n$ of about 0.55, these quantities satisfying Eq. 7. Thus, for this particular example, Nylon 101 is a suitable material for making the ellipsoidal lens. For this example, the parameters $a$ and $b$ are $a = 19.3$ cm
$b = 16.2$ cm and the focal spot and focal zone are $\delta_f = 1$mm
$\Delta f = 8$mm It is evident from the foregoing that by a suitable choice of lens material, i.e, of $\alpha$, $a$ and $b$, various distributions can be obtained. It is therefore possible to select the one material (usually plastic) whch leads to the desired focal length as well as the intensity distribution most closely approximating the desired distribution. This results in a significant simplification in transducer apodization.

A particularly practical application of the transducer according to the invention is in the pulse-echo imaging and ultrasonic neurosurgical system schematically illustrated in FIG. 3. The transducer 10, fitted with the plano-concave lens 12, is driven by suitable radio frequency driving electronics 16 and is operative to convert this electrical energy into ultrasonic waves, or to convert ultrasonic waves to radio frequency energy. Thus, the transducer is capable of acting both as an ultrasonic transmitting and detecting element, and for both functions desirably has as large an aperture as is feasible in order to maximize the ultrasound power output and the capture angle of the echoes reflected from an object, in the illustrated example, the brain of a human. The transducer is coupled to the head by a fluid medium (not shown) usually water because of its ready availability and relative ease of handling. The transducer is excited at a frequency in the range, for example, of 1–10MHz. to produce an exploratory beam when the power control 18 of the system is at the "low" position. Echo pulses detected by the transducer are applied to imaging electronics 20 tuned to the carrier frequency of the associated driving electronics to produce output voltage pulses, the magnitudes of which are proportional to the amplitude of the echo pulses. These pulses may be presented on an "A" scan display, or on the illustrated "C" scan display 22, on which the spot 24 depicts the location of the depth coordinates of an internal biological structure, such as a tumor, on the brain of the patient being examined. The transducer is movable in and out along the axis, and up and down transversely of the axis, by a suitable scanner 26.

After the coordinates of the tumor have been determined by the just-described scanning mode of the apparatus, and with the transducer and the patient maintained in such relative positions that the ultrasound beam is focussed on the tumor, the power control 18 is set to the "high" position to increase the output power level from the transducer to a level to produce a lesion (i.e., to "burn out" the tumor) at the location of the tumor. In order not to damage the surrounding tissue of the brain, the beam must be focussed to an extremely small spot size, of the order of 0.5mm and the focal zone, represented by the oval dotted line 28, should also be as small as possible. As was indicated earlier, with a F/2 elliptical lens driven at a frequency of 7MHz., it is possible to attain a spot size of 0.5mm diameter and a focal zone of about 3.6mm, this being the dimension along the axis of the transducer.

Although the illustrated and described plano-concave lens geometry is preferred because of the ease of fabrication of piezoceramic transducers in a flat configuration, and the more efficient coupling between the flat transducer element and the flat surface of the lens, the advantages of the invention are attainable with a combination of a spherically shaped transducer and a lens of sphero-elliptical shape bonded or otherwise coupled thereto.

It is evident from the foregoing description that applicants have provided, by placing a lens with plano-concave geometry in front of an ultrasonic transducer, a relatively easily fabricated and inexpensive device for generating an extremely sharply focussed beam of ultrasound which is free of spherical aberration.

We claim:

1. Apparatus for producing a spot of focussed ultrasonic energy while diminishing undesired side lobes outside the spot, comprising:
   a transducer for generating ultrasonic energy having some non-uniformity due to finite transducer size;
   a curved focusing lens operatively coupled to said transducer for focusing said ultrasonic energy at a spot on the axis of said lens;
   said lens being formed of a material which apodizes said ultrasonic energy by attenuating each ray of said energy passing therethrough in proportion to the lens thickness traversed by said ray, such that the attenuated energy combines at the focal plane to cause cancellation of side lobes outside said spot.

2. Apparatus as defined by claim 1 wherein said lens has a non-spherical ellipsoidal shape.

3. Apparatus as defined by claim 2 wherein said lens is concave.

4. Apparatus as defined by claim 1 wherein the lens material is selected such that its attenuation is a function of $(1-n)$, where $n$ is the index of refraction of the material.

5. Apparatus as defined by claim 2 wherein the lens material is selected such that its attenuation is a function of $(1-n)$, where $n$ is the index of refraction of the material.

6. Apparatus as defined by claim 3 wherein the lens material is selected such that its attenuation is a function of $(1-n)$, where $n$ is the index of refraction of the lens material.

7. Apparatus as defined by claim 2 wherein the lens material is selected such that its attenuation is proportional to $$\frac{f_\# (1-n)}{s^2 A}$$

where $f_\#$ is the numerical aperture of the apparatus, $n$ is the index of refraction of the lens material, A is the half aperture of the lens, and $s$ is a number between about 0.5 and 1.5.

8. Apparatus for producing a spot of focused ultrasonic energy, comprising:
 a transducer for generating ultrasonic energy; and
 a focusing lens operatively coupled to said transducer for focusing said ultrasonic energy at a spot on the axis of said lens, said lens having a plano-concave nonspherical ellipsoidal shape.

9. Apparatus as defined by claim 8 wherein said transducer comprises a piezoelectric disc.

* * * * *